United States Patent [19]
Demers et al.

[11] Patent Number: 4,820,828
[45] Date of Patent: Apr. 11, 1989

[54] CINNAMOHYDROXAMIC ACIDS

[75] Inventors: James P. Demers, New York, N.Y.; William V. Murray, Belle Mead; Richard B. Sulsky, Somerville, both of N.J.

[73] Assignee: Ortho Pharmaceutical Corporation, Raritan, N.J.

[21] Appl. No.: 21,819

[22] Filed: Mar. 4, 1987

[51] Int. Cl.$^4$ .................. C07D 319/18; C07D 317/52
[52] U.S. Cl. .................... 549/362; 549/441; 260/500.5 H; 514/452; 514/466
[58] Field of Search .............. 549/362, 441; 260/500.5 H

[56] References Cited

U.S. PATENT DOCUMENTS

| | | | |
|---|---|---|---|
| 4,188,338 | 2/1980 | Bruins et al. | 260/500.5 H |
| 4,608,390 | 8/1986 | Summers, Jr. | 514/575 |
| 4,623,661 | 11/1986 | Summers, Jr. | 514/575 |

FOREIGN PATENT DOCUMENTS 0196184  1/1986  European Pat. Off. .
0199151  10/1986  European Pat. Off. .

OTHER PUBLICATIONS

Nakonieczna et al., Chem. Abs., 104, 149372w, (1986).
Tanaka et al., Chem. Pharm. Bull., 31, 2810, (1983).
Kehl et al., Arzneim.-Forsch., 28, 2087-2092, (1978).
Buu-Hoi et al., J. Med. Chem., 13, 211, (1970).

Primary Examiner—John W. Rollins
Assistant Examiner—W. Catchpole
Attorney, Agent, or Firm—Benjamin F. Lambert

[57] ABSTRACT

The present invention relates to cinnamohydroxamic acids. These compounds inhibit 5-lipoxygenase and are useful as bronchodilators.

2 Claims, No Drawings

CINNAMOHYDROXAMIC ACIDS

BACKGROUND OF THE INVENTION

1. Field of the Invention

The present invention relates to cinnamohydroxamic acids as described further below. These compounds inhibit 5-lipoxygenase and are useful as bronchodilators.

2. Description of the Prior Art

N-unsubstituted cinnamohydroxamic acids have been described in the prior art. These include 3-substituted-4-alkoxycinnamohydroxamic acids wherein the 3 substituent may be hydrogen, halogen or alkoxy. See Buu-Hoi et al., *J.Med.Chem.* 13, 211 (1970). The compounds are said to have weak anti-inflammatory activity, and some compounds demonstrate antispasmodic activity. Tanaka et al., *Chem.Pharm.Bull.* 31, 2810 (1983) describe 4-methoxy-, 4-chloro-, 4-nitro- or 3,4-dimethoxy-cinnamohydroxamic acids which have anti-inflammatory and analgesic activity. Belgian Pat. No. 701,983 discloses substantially the same set of compounds, with the same utility, i.e., antiphlogistic, analgesic and antipyretic activity. French Pat. No. 1,461,338 describes some 3,4,5-trimethoxycinnamohydroxamic acids as "pharmaceutical intermediates".

Two references describe compounds which may be considered prodrugs of the above compounds. Paynard et al., *Eur.J.Med. Chem.* 10, 125 (1975) and French Pat. No. 2,190,430 describe various N-(dialkylaminomethyl)cinnamohydroxamic acids, with similar biological activities and potencies.

Szilagyi et al., *Acta Pharm.Hung.* 45, 49 (1975) discloses 3,5-dichloro-4-methoxy- and 3,5-methoxy-4-octyloxycinnamohydroxamic acids which were reported as having central nervous system (CNS) activity.

4-Acyl-2-alkyl-3-hydroxycinnamohydroxamic acids fall under the broad claims of European Pat. No. 132,366, which describes leukotriene antagonists useful for treating allergic disorders.

Similarly, N-substituted cinnamohydroxamic acids have also been described in the prior art. The N-methyl and N-t-butyl, ring-unsubstituted compounds have been disclosed. The former has been reported to be a vasodilator by Kehl et al., *Arzneim.-Forsch.* 28, 2087 (1978), while the latter was prepared by Jenkins et al., *J.Chem.-Soc.Perkin Trans.* 2, 717 (1983) for physical-chemical studies. In addition, the N-(aminomethyl) derivatives (described above) and 3,4-dimethoxy-N-methylcinnamohydroxamic acid, prepared as an intermediate by Fountain et al. in *Chem. and Biol. of Hydroxamic Acids,* Proceedings of the First International Symposium, H. Kehl, ed., Karger (Basel), pp. 51–62 (1982) have been disclosed in the prior art. The broad claims of European Pat. No. 132,366 (described above) include N-alkyl derivatives. A few N,O-dialkylcinnamohydroxamic acids are claimed as CNS depressants in French Pat. No. 1,332,352.

Finally, several references describe compounds which have been disclosed to inhibit lipoxygenases. U.S. Pat. Nos. 4,623,661, 4,605,669 and 4,608,380, as well as European Pat. No. 199,151, describe compounds having the formula

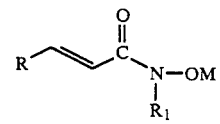

where R is a trinuclear aromatic group, a binuclear aromatic group or a substituted naphthyl group.

European Pat. No. 196,184 describes an exceedingly vast array of compounds which may include cinnamohydroxamic acids, such as N,4-methylcinnamohydroxamic acid. The generic disclosure includes compounds of the above formula where R is phenyl or phenyl substituted by alkyl, alkoxy, halogen, nitro, amino or hydroxy. Although the compounds are said to be useful in treating a large variety of disorders (see column 13, line 21—column 14, line 36 and column 15, line 1—column 18, line 4), no specific disclosure of activity other than for cut flowers is provided.

SUMMARY OF THE INVENTION

The present invention is directed to cinnamohydroxamic acids of the formula

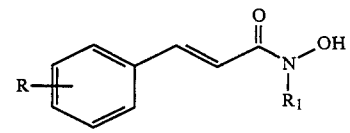

where R may be H, $C_1$–$C_6$ alkyl, $C_1$–$C_6$ alkoxy, $NO_2$, $NH_2$, F, Cl, Br, I, hydroxy, or

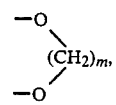

where m is 1 or 2 and the alkylenedioxy group is attached to adjacent carbon atoms on the phenyl ring and $R_1$ may be H, $C_1$–$C_6$ alkyl or $C_3$–$C_6$ cycloalkyl.

The present invention is also directed to the treatment of the symptoms of asthma and other obstructive airway diseases with agents that inhibit 5-lipoxygenase, the first enzyme in the biochemical pathway leading to the bronchoconstricting and chemotactic leukotrienes. The treatment of asthma with bronchodilators is well established, but agents acting by inhibition of the allergen-induced bronchospasm would be an important addition to the therapy of asthma. The cinnamohydroxamic acids of the present invention are simultaneously bronchodilators and 5-lipoxygenase inhibitors.

DETAILED DESCRIPTION OF THE INVENTION

The invention in its broadest aspects relates to cinnamohydroxamic acids which are inhibitors of 5-lipoxygenase and have bronchodilating activity. The cinnamohydroxamic acids demonstrating 5-lipoxygenase inhibitory activity and bronchodilating activity are shown by formula I above. The phenyl ring may be unsubstituted, mono-substituted or poly-substituted.

The preferred compounds of the present invention are those where $R_1$ is H or $CH_3$ and the phenyl ring is polysubstituted, that is, by two or more R groups which may be same or different.

The compounds of formula I where $R_1$ is other than H can be prepared by reacting a cinnamoyl chloride of the formula

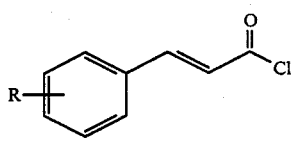

or a mixed anhydride of the formula

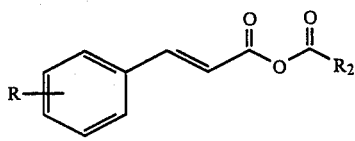

where $R_2$ is t-butyl or ethoxy with an N-substituted hydroxylamine in an inert solvent in the presence of a base at about $-30°$ C. to about $40°$ C. for about 0.25–16 hours. Suitable inert solvents include dichloromethane, dimethylformamide, tetrahydrofuran and the like. The base may be sodium carbonate, triethylamine and the like, preferably triethylamine.

The compounds of formula I where $R_1$ is H can be prepared by reacting hydroxylamine with a compound of the formula

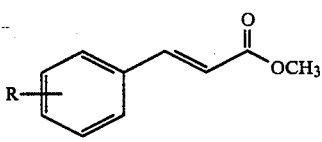

in an alcoholic base below 40° C. for about 1–2 hours. A suitable base is potassium hydroxide and a suitable alcohol is methanol.

The compounds of formula I relieve the symptoms of asthma by two mechanisms: as bronchodilators and by inhibiting the synthesis of leukotrienes. To our knowledge, currently available bronchodilators do not possess this activity against leukotrienes. Since leukotrienes are believed to be involved in the chemotaxis of inflammatory cells, and it is well established that the leukotrienes are potent bronchospastic agents, inhibition of their synthesis would provide symptomatic relief of the bronchospasm and prevent further deterioration of the individual by preventing the progression of the inflammation. The added bronchodilating properties, separate from the effects on leukotrienes, should aid in their effectiveness.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.01 to about 100 mg/kg, and preferably from about 0.1 to about 50 mg/kg of the active ingredient.

The following examples describe the invention in greater particularity and are intended to be a way of illustrating but not limiting the invention.

EXAMPLE 1

4-Fluoro-N-methylcinnamohydroxamic acid

A solution of 4-fluorocinnamic acid (2.0 g, 12 mmol), oxalyl chloride (1.65 g, 13 mmol) and N,N-dimethylformamide (four drops) in 40 ml dichloromethane was stirred overnight under nitrogen. The resulting solution was evaporated in vacuo, and the resulting solid redissolved in 10 ml dichloromethane. The resulting solution of 4-fluorocinnamoyl chloride was added dropwise to a cold (5°–10° C.), stirred mixture prepared from N-methylhydroxylamine hydrochloride (1.09 g, 13 mmol) and triethylamine (5 ml, 35 mmol), which had been stirred for 20 minutes. The reaction mixture was allowed to warm to room temperature, then washed successively with aqueous 1N HCl and 1N NaHCO$_3$. The organic solution was then chromatographed on silica gel with 2% isopropanol in dichloromethane. The product was recrystallized from methanol-water, to provide 1.65 g of the titled compound as a white powder, mp 141°–141.5° C.

EXAMPLE 2

2,5-Dimethoxy-N-methylcinnamohydroxamic acid

A solution of 2,5-dimethoxycinnamic acid (2.08 g, 10 mmol), oxalyl chloride (0.96 ml, 11 mmol) and N,N-dimethylformamide (two drops) in 25 ml dichloromethane was stirred for 20 minutes. The resulting solution was evaporated to leave a yellow solid, which was then dissolved in 10 ml of acetone. This solution was added slowly to a stirred mixture of water (20 ml), sodium carbonate (2.5 g, 24 mmol), and N-methylhydroxylamine hydrochloride (1.06 g, 12.7 mmol), cooled to 5° C. The resulting mixture was stirred for 20 minutes, then poured into excess 1M hydrochloric acid and extracted twice with ethyl acetate. The extracts were washed wth water and 1N NaHCO$_3$, dried over MgSO$_4$, and evaporated to leave an orange oil. Chromatography on silica gel with 7:3 ethyl acetate-hexane provided 0.96 g (40% yield) of the named compound, mp 111°–112° C., after recrystallization from hexane-1,2-dichloroethane.

EXAMPLE 3

3,4,5-Trimethoxy-N-methycinnamohydroxamic acid

Triethylamine (3.07 ml, 22 mmol) was added to a stirred solution of 3,4,5-trimethoxycinnamic acid (4.76 g, 20 mmol) in N,N-dimethylformamide (30 ml). The resulting solution was cooled to −12° C., and ethyl chloroformate (2.00 ml, 21 mmol) was added dropwise with stirring. After 15 minutes, solid N-methylhydroxylamine hydrochloride (1.84 g, 22 mmol) was added, followed by triethylamine (3.2 ml, 23 mmol). The mixture was allowed to warm to room temperature, stirred overnight, and poured into 150 ml of 1% aqueous citric acid. The mixture was extracted twice with ethyl ether, and the combined extracts washed successively with water and brine, then dried over $MgSO_4$, filtered, and evaporated. The residue was recrystallized from ethyl acetate to provide 1.82 g (34% yield) of the titled compound as colorless crystals, mp 169°–170° C.

EXAMPLE 4

3,4-Dimethoxy-N-methylcinnamohydroxamic acid

Pivaloyl chloride (23.5 g, 195 mmol) was added dropwise to a stirred solution of 3,4-dimethoxycinnamic acid (40 g, 192 mmol) and triethylamine (54.4 ml, 390 mmol) in N,N-dimethylformamide (600 ml) at −30° C. To the resulting mixture was added a solution of N-methylhydroxylamine hydrochloride (15.9 g, 190 mmol) in N,N-dimethylformamide (50 ml). The mixture was allowed to warm slowly to room temperature. Ethyl ether (600 ml) was added, and the precipitated triethylamine hydrochloride filtered off. The filtrate was concentrated in vacuo to leave a yellow oil, which was dissolved in 400 ml ethyl acetate. Additional triethylamine hydrochloride was removed by filtration, and the filtrate seeded and allowed to stand at room temperature overnight. The precipitated product was collected by filtration, dried in vacuo, and recrystallized from methanol-water to provide 19.0 g of the named compound as a white powder, mp 149.5°–150.5° C.

EXAMPLE 5

4-Chloro-3-hydroxy-N-methylcinnamohydroxamic acid

A solution of 4-chloro-3-hydroxycinnamic acid (1.0 g, 5.0 mmol) in N,O-bis(trimethylsilyl)acetamide (2.5 g, 12.3 mmol) was prepared by gentle heating. The resulting solution was concentrated in vacuo to leave crude bis-silylated material. This residue was dissolved in dichloromethane (15 ml) and oxalyl chloride (0.76 g, 6.0 mmol) and N,N-dimethylformamide (two drops) were added. The resulting solution was stirred under nitrogen at room temperature for 20 minutes, then concentrated in vacuo to leave crude 4-chloro-3-trimethylsiloxycinnamoyl chloride as a yellow oil. This was dissolved in dichloromethane (15 ml), and added dropwise to a stirred solution of triethylamine (2.3 ml, 16.5 mmol) and N-methylhydroxylamine hydrochloride (0.45 g, 5.4 mmol) in dichloromethane (20 ml). The solvent was removed in vacuo, and the residue refluxed for two minutes in 20 ml methanol to desilyate the product. The solvent was removed in vacuo, and the residue dissolved in 10 ml dichloromethane. Methyl t-butyl ether (50 ml) was added, the triethylamine hydrochloride removed by filtration, and the filtrate chromatographed on silica gel with 5% and then 10% isopropanol in dichloromethane. Recrystallization of the product from methanol-water provided 0.52 g (46% yield) of the titled compound as a white powder, mp 196°–196.5° C.

EXAMPLE 6

3,4-Dimethoxycinnamohydroxamic acid

A solution of hydroxylamine hydrochloride (5.09 g, 72 mmol) in methanol (26 ml) was added to a solution of 88% potassium hydroxide (6.99 g, 109 mmol) in methanol (15.3 ml), keeping the temperature below 40° C. The mixture was cooled to 0° C., filtered, and methyl 3,4-dimethoxycinnamate (8.0 g, 36 mmol) was added to the filtrate. After two hours, concentrated HCl (5 ml) was added to the cold solution. The resulting precipitate was filtered, washed with water and ether, and dried in vacuo, to give 6.74 g (84% yield) of the named compound, mp 183°–185° C.

EXAMPLE 7

N,4-Dimethylcinnamohydroxamic acid

A solution of 4-methylcinnamic acid (1.62 g, 10 mmol) and oxalyl chloride (2.0 ml, 23 mmol) in 50 ml anhydrous tetrahydrofuran (THF) was stirred at reflux for two hours, then concentrated in vacuo. The residue was redissolved in 30 ml THF, and added dropwise to a solution of N-methyl-hydroxylamine hydrochloride (1.26 g, 15 mmol) and triethylamine (5.0 ml, 36 mmol) in 50 ml of 2:1 THF-water at 0° C. The mixture was stirred for one hour at 0° C., then for one hour at room temperature, and then poured into excess 5% aqueous hydrochloric acid. The resulting mixture was extracted with ethyl ether, and the ether extract washed successively with 5% aqueous hydrochloric acid and brine, dried over sodium sulfate, and evaporated. Recrystallization of the residue from ethyl acetate provided 1.48 g (77% yield) of the titled compound, mp 142°–144° C.

EXAMPLES 8-27

The cinnamohydroxamic acids of Examples 8–27 were prepared by following the procedures of the preceding examples, as shown in Table I, using the appropriate cinnamic acid as the starting material.

TABLE I

| Example | Title Compound, mp | Procedure of Example |
|---|---|---|
| 8 | 2-Methoxy-N—methylcinnamohydroxamic acid, mp 123°–125° C. | 4 |
| 9 | Cis-2-methoxy-N—methylcinnamohydroxamic acid, mp 87°–89° C. | 4 |
| 10 | 3,5-Dimethoxy-4-hydroxy-N—methylcinnamohydroxamic acid, mp 127°–129° C. | 5 |
| 11 | 4-Chloro-2-methoxy-N—methylcinnamohydroxamic acid, mp 96°–96.5° C. | 4 |
| 12 | 3,4-Methylenedioxy-N—methylcinnamohydroxamic acid, mp 177°–179° C. | 4 |
| 13 | 3,4-(1,2-Ethylenedioxy)-N—methylcinnamohydroxamic acid, mp 130°–131.5° C. | 4 |
| 14 | 2,4-Dichloro-N—methylcinnamohydroxamic acid, mp 148°–149° C. | 4 |
| 15 | 2,6-Dichloro-N—methylcinnamohydroxamic acid, mp 135°–136° C. | 4 |
| 16 | 3,4-Dichloro-N—methylcinnamohydroxamic acid, mp 157°–159° C. | 2 |
| 17 | N—Methylcinnamohydroxamic acid, mp 135°–136° C. | 4 |
| 18 | 3,5-Dimethoxy-N—methylcinnamohydroxamic acid, mp 101°–102° C. | 2 |
| 19 | 2,3-Dimethoxy-N—methylcinnamohydroxamic acid, mp 81°–83° C. | 2 |
| 20 | 2,4-Dimethoxy-N—methylcinnamohydroxamic acid, mp 115°–116° C. | 2 |
| 21 | 3,4-Dimethoxy-N—t-butylcinnamohydroxamic acid, mp 131°–133° C. | 1 |
| 22 | 2,6-Dimethoxy-N—methylcinnamo- | 1 |

TABLE I-continued

| Example | Title Compound, mp | Procedure of Example |
|---|---|---|
|  | hydroxamic acid, mp 136°–137° C. |  |
| 23 | 4-Chloro-3-nitro-N—methylcinnamo-hydroxamic acid, mp 145°–146° C. | 1 |
| 24 | 3-Methoxy-N—methylcinnamo-hydroxamic acid, mp 87°–89° C. | 4 |
| 25 | 4-Methoxy-N—methylcinnamo-hydroxamic acid, 148°–150 ° C. | 7 |
| 26 | 4-Chloro-N—methylcinnamo-hydroxamic acid, mp 152°–154° C. | 7 |
| 27 | 3,5-Di-t-butyl-4-hydroxy-N—methyl-cinnamo-hydroxamic acid, mp 157°–159° C. | 7 |

By substituting 2-chloro-, 3-chloro-, 2-fluoro-, 3-bromo- or 4-bromocinnamic acid in the above examples, the corresponding 2-chloro-, 3-chloro-, 2-, fluoro-, 3-bromo- or 4-bromocinnamohydroxamic acids are obtained.

By substituting N-isopropyl or N-cyclohexyl-hydroxylamine in the above examples, the corresponding N-isopropyl- or N-cyclohexyl-cinnamohydroxamic acids are obtained.

EXAMPLE 28

Inhibition of 5-lipoxygenase

The inhibition of 5-lipoxygenase was tested in a cell-free homogenate by the procedure of Jakschik, B. et al., *Biochem.Biophys.Res.Comm.* 95, 103 (1980). Basically, rat basophilic leukemia cells (RBL-1 cells) were maintained in culture in a suitable medium, and were collected by centrifugation prior to assay. The cell-free homogenate was prepared by sonication of the cells followed by centrifugation at 40,000 xg. The $CaCl_2$ dependent production of lipoxygenase products from $^{14}C$-arachidonic acid in the 40,000 xg supernatant was monitored in the presence of buffer (or other vehicle) or drug. Products were isolated by acidification and extraction, followed by thin layer chromatography. Radioactive areas corresponding to authentic lipoxygenase products were quantitated by liquid scintillation counting. Data was reported as the $IC_{50}$, the concentration causing 50% inhibition of the generation of lipoxygenase products. The results are shown in Table II as the percent inhibition at 3 μM or the amount of compound necessary to cause 50% inhibition.

EXAMPLE 29

Pulmonary Mechanics Assay

The bronchodilating activity of the compounds was tested in a pulmonary mechanics assay. Basically, male Hartley guinea pigs (~400–500 g) were anesthetized with urethane (2 g/kg, i.p.) and placed in a whole body plethysmograph. Cannulations of a jugular vein and carotid artery were performed for compound administration and monitoring blood presure, respectively. The trachea was cannulated for respiration at a constant volume via a miniature starling pump. A Validyne differential pressure transducer (±20 cm $H_2O$) sensed transpleural pressure via a 15 gauge needle inserted into the pleural cavity and a sidearm from the tracheal cannula. Tidal volume was sensed by another Validyne differential pressure transducer (±2 cm $H_2O$) from pressure changes inside the plethysmograph. An on-line Buxco pulmonary mechanics computer calculated air flow, dynamic lung compliance and lung resistance. The values were recorded on a print-out.

The guinea pigs were pretreated with succinyl choline (1.2 mg/kg, i.v.) to arrest spontaneous respiration. A control challenge of arachidonic acid (0.5–1.0 mg/kg, i.v.) was administered, and the animals were then dosed with the test compound by various routes. At least 10 minutes were allowed to expire between arachidonic acid challenges. A second challenge was given and compared to the control response. This comparison was indicative of cyclooxygenase inhibition. Indomethacin (10 mg/kg, i.v.) was administered immediately after the second challenge. A third challenge of a higher dose of arachidonic acid (5–10 mg/kg, i.v.) was given. This response was induced by SRS-A and compared to the responses elicited by a separate control group of animals. Activity was indicative of lipoxygenase inhibition. Propranolol (0.005 mg/kg, i.v.) may be given prior to the third challenge to enhance the response to SRS-A.

Bronchoconstriction induced by arachidonic acid with or without indomethacin was expressed as maximum percent change in dynamic lung compliance (Cdyn) and maximum percent increase in lung resistance ($R_L$). Each guinea pig served as its own control for cyclooxygenase evaluation, while a treated group was compared to a control group for lipoxygenase evaluation. The results are shown in Table II and are expressed as the percent inhibition of control.

TABLE II

| Example | Inhibition of 5-lipoxygenase % at 3 μM | Inhibition of 5-lipoxygenase $IC_{50}(\mu M)$ | Bronchodilating Activity % Inhibition of Arachidonate Induced Bronchospasm with/without Indomethacin | Dose (mg/kg) (Route) |
|---|---|---|---|---|
| 1 | 30 |  |  |  |
| 2 | 53 |  | 49/65 | 15 (IV) |
| 3 | 91 |  | 89/00 | 15 (IV) |
| 4 | 89 | 0.6 | 90/82 | 15 (IV) |
| 5 | 35 |  |  |  |
| 6 | 17 |  | 61/77 | 10 (ID) |
| 7 |  | 0.55 | 89/96 | 15 (IV) |
|  |  |  | 0/59 | 100 (ID) |
| 8 | 66 |  | 73/94 | 15 (IV) |
|  |  |  | 58/−76 | 50 (ID) |
| 9 | 59 |  | 36/29 | 15 (IV) |
| 10 | 17 |  |  |  |
| 12 | 53 |  | 58/15 | 15 (IV) |
| 13 | 53 |  |  |  |
| 14 | 88 |  |  |  |
| 15 | 24 |  |  |  |
| 16 | 87 |  | 86/62 | 15 (IV) |
| 17 | 50 |  | 0/−35 | 50 (ID) |
| 18 | 100 |  | 78/48 | 15 (IV) |
| 19 | 44 |  | 70/34 | 15 (IV) |
| 20 | 100 | 0.43 | 46/46 | 25 (ID) |
| 22 | 41 |  |  |  |
| 23 | 30 |  |  |  |
| 24 | 54 |  | 66/28 | 15 (IV) |
|  |  |  | 49/0 | 50 (ID) |
| 25 |  | 1.3 | 29/00 | 15 (IV) |
| 26 |  |  | 70/87 | 15 (IV) |
| 27 | 65 |  | 89/56 | 15 (IV) |

What is claimed is:

1. A compound of the formula

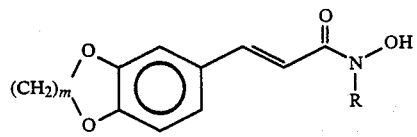

wherein R, is hydrogen; $C_1$–$C_6$-lower alkyl; or $C_3$–$C_6$-cycloalkyl; and m is 1 or 2.

2. A compound of claim 1 selected from the group consisting of 3,4-methylenedioxy-N-methylcinnamohydroxamic acid and 3,4-(1,2-ethylenedioxy)-N-methylcinnamohydroxamic acid.

* * * * *